United States Patent
Schenck

(10) Patent No.: US 8,721,701 B2
(45) Date of Patent: May 13, 2014

(54) VASCULAR OCCLUSION DEVICE DEPLOYMENT SYSTEM WITH GRIPPING FEATURE OPENED BY A COLLAPSIBLE REACTION CHAMBER

(75) Inventor: Jessica T. Schenck, Waltham, MA (US)

(73) Assignee: Depuy Synthes Products, LLC, Raynham, MA (US)

( * ) Notice: Subject to any disclaimer, the term of this patent is extended or adjusted under 35 U.S.C. 154(b) by 2242 days.

(21) Appl. No.: 11/383,995

(22) Filed: May 18, 2006

(65) Prior Publication Data

US 2007/0270930 A1  Nov. 22, 2007

(51) Int. Cl.
*A61F 2/06* (2013.01)
*A61F 2/02* (2006.01)

(52) U.S. Cl.
USPC ........ 623/1.11; 623/23.72; 606/200; 606/213

(58) Field of Classification Search
USPC ............. 606/200, 108, 205, 7, 213; 623/1.23, 623/1.11, 1.12, 23.72; 604/145; 92/89–93
See application file for complete search history.

(56) References Cited

U.S. PATENT DOCUMENTS

| | | | |
|---|---|---|---|
| 3,574,381 A | 4/1971 | Ocheltree | |
| 4,728,217 A | 3/1988 | Fink | |
| 4,909,789 A | 3/1990 | Taguchi et al. | |
| 5,062,847 A | 11/1991 | Barnes | |
| 5,108,407 A | 4/1992 | Geremia et al. | |
| 5,609,608 A | 3/1997 | Benett et al. | |
| 5,783,130 A | 7/1998 | Benett et al. | |
| 5,814,062 A * | 9/1998 | Sepetka et al. | 606/198 |
| 5,827,304 A | 10/1998 | Hart | |
| 5,861,035 A | 1/1999 | Griffith | |
| 5,941,895 A | 8/1999 | Myler et al. | |
| 5,989,242 A | 11/1999 | Saadat et al. | |
| 6,187,016 B1 | 2/2001 | Hedges et al. | |
| 6,361,547 B1 * | 3/2002 | Hieshima | 606/200 |
| 6,371,469 B1 | 4/2002 | Gray | |
| 6,478,773 B1 | 11/2002 | Gandhi et al. | |
| 6,692,504 B2 | 2/2004 | Kurz et al. | |
| 6,783,530 B1 | 8/2004 | Levy | |
| 6,802,846 B2 | 10/2004 | Hauschild et al. | |
| 7,357,809 B2 * | 4/2008 | Jones et al. | 606/205 |
| 7,582,101 B2 * | 9/2009 | Jones et al. | 606/200 |

* cited by examiner

*Primary Examiner* — Dianne Dornbusch

(74) *Attorney, Agent, or Firm* — Cook Alex Ltd.

(57) ABSTRACT

A vascular occlusion device deployment system for placing an occlusion device at a preselected site within the vasculature of a patient. The deployment system employs a pusher including a gripper located at the distal end of the pusher to releasably retain a vascular occlusion device. The gripper is expanded under the force of a collapsible chemical reaction chamber so that the gripper releases the vascular occlusion device, thereby deploying the vascular occlusion device.

13 Claims, 1 Drawing Sheet

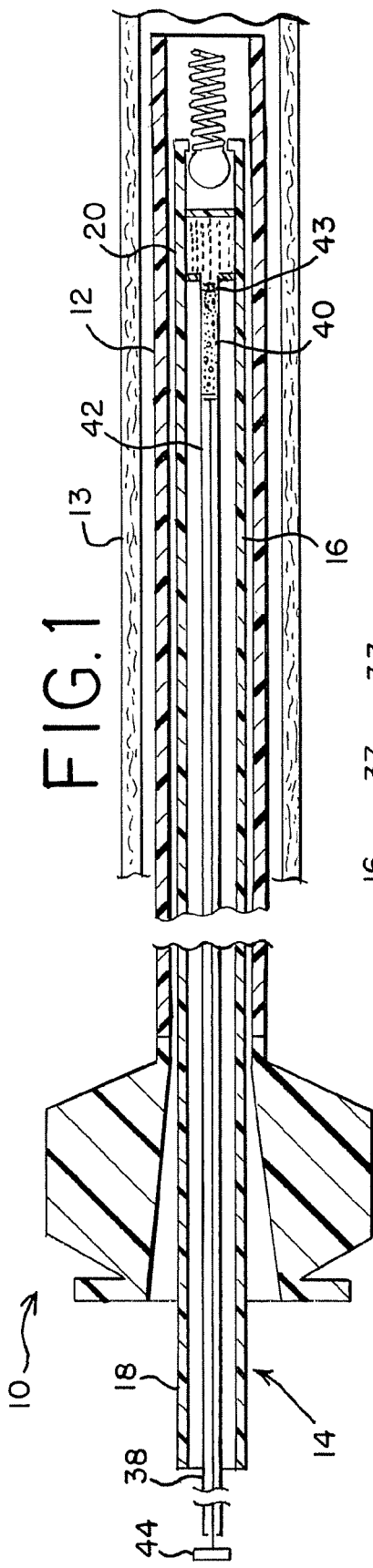
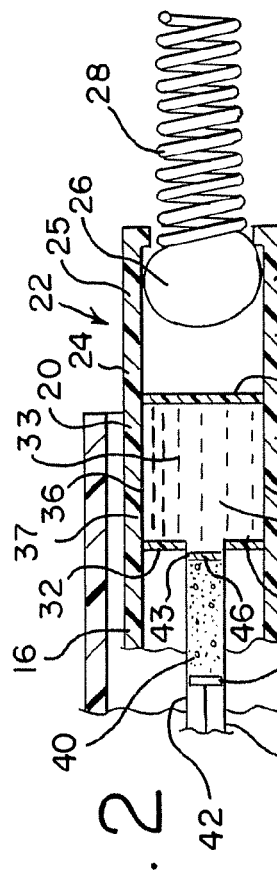
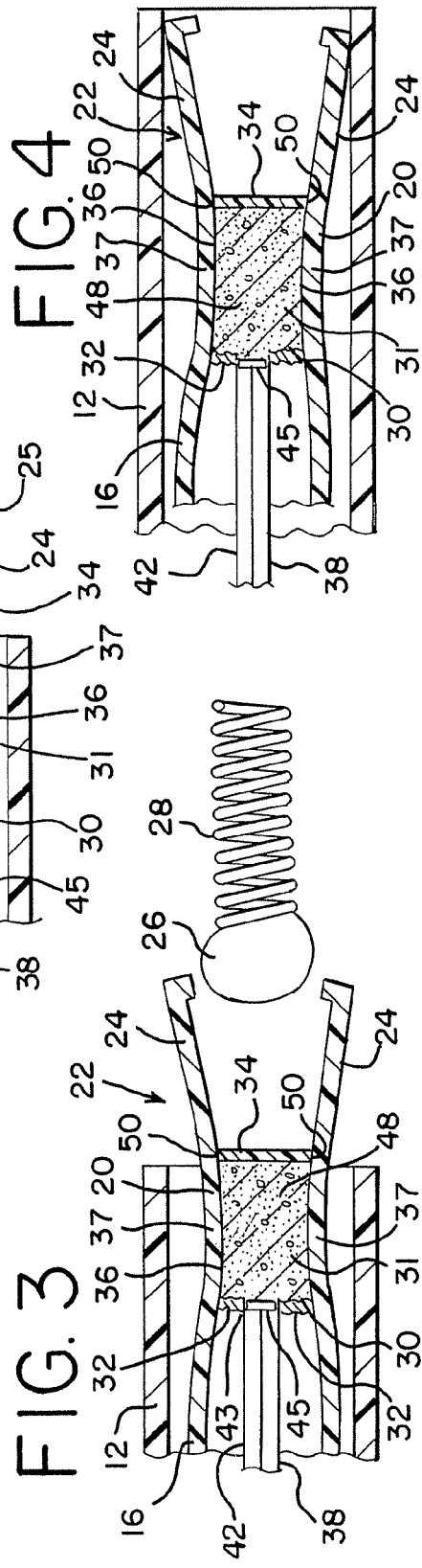
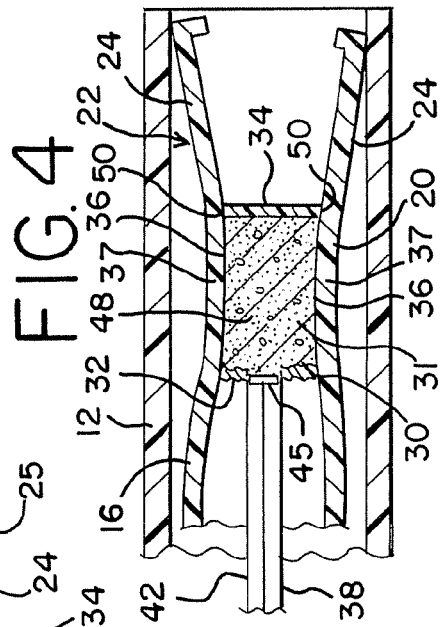
FIG. 1
FIG. 2
FIG. 3
FIG. 4

VASCULAR OCCLUSION DEVICE DEPLOYMENT SYSTEM WITH GRIPPING FEATURE OPENED BY A COLLAPSIBLE REACTION CHAMBER

FIELD OF THE INVENTION

The present invention is related to deployment systems and methods for accurately and rapidly deploying vascular occlusion devices at a preselected location within the vascular system of a patient, and more particularly, deployment approaches that utilize a pusher having an expandable gripper which is opened by the action of a collapsible chemical reaction chamber to facilitate rapid deployment of vascular occlusion devices.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in intracranial blood vessels. Due to the delicate tissue surrounding intracranial blood vessels, especially for example brain tissue, it is very difficult and often risky to perform surgical procedures to treat such a defect. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to the accuracy of coil placement. For example, the force of the coil exiting the delivery catheter may cause the coil to over shoot the predetermined site or dislodge previously deployed coils. Also, once the coil is pushed out of the distal end of the catheter, the coil cannot be retracted and may migrate to an undesired location. Often, retrieving and repositioning the coil requires a separate procedure and has the potential to expose the patient to additional risk.

In response to the above mentioned concerns, numerous devices and release mechanisms have been developed in an attempt to provide a deployment system which allows control of the occlusion device after the device has been delivered by the catheter and provides a rapid release or detachment mechanism to release the device once it is in place. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that interfere with other surgical and/or monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transmits the light into heat energy. The heat energy raises the temperature of the connector and opens the fingers, thereby releasing the embolic coil. This delivery system and the other above-identified delivery systems require electronic equipment powered by a power source. If the electronic equipment is defective or the power source fails, for example a battery pack fails, the procedure may be prolonged while the equipment is repaired or replaced. Prolonging the procedure may expose the patient to additional risk. This patent, and all other patents and references identified herein are hereby incorporated herein by reference.

Therefore, a need remains for a rapid release vascular occlusion deployment system or method that does not rely on electrical equipment or a power supply, is simple to manufacture, flexible and easy to guide through the vasculature of the body, provides better control over the occlusion device, and reduces the possibility of interference with other surgical and/or monitoring equipment.

SUMMARY OF INVENTION

The present invention embodies deployment systems and methods for accurately and rapidly deploying a vascular occlusion device at a preselected site within the vasculature of a patient. The deployment system may employ an elongated flexible delivery catheter for guiding a deployment unit to the preselected site. The deployment unit includes a pusher which has a gripper located at a distal end portion of the pusher. The gripper has an expandable gripping element, for example a plurality of gripping jaws, for releasably attaching a vascular occlusion device, such as an embolic coil, to the deployment system. The pusher guides the vascular occlusion device through the delivery catheter to the preselected site.

A collapsible or contractible reaction chamber operatively communicates with the gripper. A first reactant is housed within the collapsible reaction chamber. The delivery system also includes a dispensing unit for dispensing a second reactant into the reaction chamber. When the second reactant is dispensed into the chamber, the first and second reactants react to form a product that has a volume that is less than the volume of the first reactant prior to reacting. The reduction of the volume occupied by the substances inside of the reaction chamber causes the pressure within the reaction chamber to decrease which results in a collapse of the reaction chamber. As the reaction chamber collapses, it pulls the proximal end of the gripping element inward causing the distal end of the gripping element to outwardly expand or open so that the gripping element releases the vascular occlusion device, thereby deploying the vascular occlusion device at the preselected location.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 1 is an enlarged, partially sectioned view of the vascular occlusion device deployment system of a preferred embodiment of the present invention;

FIG. 2 is an enlarged partially sectioned view showing the distal end portion of the deployment system of FIG. 1 prior to deployment of the occlusion device;

FIG. 3 is an enlarged partially sectioned view of the distal end portion of the deployment system of FIG. 1 shown just after deployment of the vascular occlusion device; and FIG. 4 is an enlarged partially sectioned view of the distal end portion of the deployment system of FIG. 1 shown after deployment of the vascular occlusion device.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 generally illustrates a preferred embodiment of the vascular occlusion device deployment system of the present invention. The deployment system, generally designated at 10, includes an elongated flexible guiding catheter 12 which is inserted into the vascular system of a patient, such as blood vessel 13, and used to guide a deployment unit, generally designed 14, to a preselected site in a manner generally known in the art. The deployment unit 14 includes an elongated flexible pusher or delivery tube 16 having a proximal end portion 18 and a distal end portion 20.

As best illustrated in FIG. 2, a gripper 22 is located at the distal end portion 20 of the pusher 16. The gripper 22 includes an outwardly expandable gripping element 24, which is generally illustrated as a plurality of jaws 25. Typically, the gripping element 24 and the jaws 25 will be not occupy the full circumference of the distal end portion 20 and the jaws 25 may, for example, take the form of two fingers protruding distally. The gripping element 24 releasably engages a protruding portion or headpiece 26 of a vascular occlusion device 28, such as an embolic coil. As will be discussed in more detail below, when the gripping element 24 expands outwardly or opens, it releases the headpiece 26 of the vascular occlusion device 28.

The gripper 22 may be comprised of polymer, such as FEP Teflon, PTFE Teflon, polyvinyl chloride, a polyolefin or a neoprene, or any other suitable polymer, and may be constructed as disclosed in Bennett et al. U.S. Pat. No. 5,609,608, hereby incorporated herein by reference. Alternatively, the gripper 22 may be constructed of any suitable metal, or the gripper could comprise a microtube which has been slit. A suitable microtube may be made of stainless steel or of a nickel-titanium alloy such as Nitinol, or other suitable material. Further, in the illustrated embodiment, the gripper 22 and pusher 16 are shown as a unitary structure. However, it will be understood that the gripper 22 could be a separate unit which is attached to the pusher 16 in any suitable manner, for example by a silicone or cyanoacrylate adhesive.

As stated above, the occlusion device 28 may be an embolic coil which may take various forms and configurations, and may also be filled with a fibrous material or may be coated with a beneficial substance, such as a biogel to promote clotting. Alternatively, the occlusion device also may be any other occlusion device or approach known in the art such as hydrogels, foams, bioactive coils, braids, cables, and hybrid devices.

A collapsible or contractible reaction chamber 30 is positioned in the distal end portion 20 of the pusher 16, preferably within the gripper 22. The reaction chamber 30 comprises a cavity 31 that houses a first reactant 33 which is preferably a gas or a liquid. The cavity 31 is defined by a proximal wall 32, a distal wall 34 and inner surface 36 of a sidewall 37 of the cavity 31. The sidewall 37 is constructed such that it will deform inwardly or collapse in response to forces acting on it that are generated as described herein. In the embodiment where the jaws 25 are relatively narrow, the sidewall 37 can have an area of weakness in general alignment therewith to facilitate movement of the jaws during operation as described herein. The first reactant 33 occupies the defined volume of the cavity 31. This can be considered to create a pressure within the chamber 30 that is equal to or slightly higher than the external pressure outside of the chamber.

The proximal wall 32 and distal wall 34 are preferably comprised of an elastic membrane which may be attached to the inner surface 36 of the gripper 22 by an adhesive, such as a cyanoacrylate adhesive, or by any other suitable manner. The elastic membranes may be constructed from materials that do not significantly degrade while in contact with the reactant materials or the product formed therefrom. Typically, these will be an elastic polymer, such as silicone, a polyamide, a nylon, or a polyolefin such as polyethylene. Furthermore, the respective membranes will have different Durometer hardness values. For reasons that will be discussed in more detail below, the proximal wall 32 preferably is made of a lower Durometer polymer which can be easily flexed or bent in response to changes of pressure within the reaction chamber 30. On the other hand, the distal wall 34 preferably is made from a higher Durometer polymer that resists bending or flexing in response to changes of pressure within the chamber 30.

The delivery unit 14 also includes a dispensing unit 38 for dispensing a second reactant 40 into the cavity 31 of the reaction chamber 30. The illustrated dispensing unit 38 comprises a plunger-activated dispensing tube 42 which extends within the pusher 16 from the proximal end portion 18 to the distal end portion 20 of the pusher 16. A distal end portion 43 of the dispensing tube 42 extends through the proximal wall 32 of the reaction chamber 30 into the cavity 31. The proximal wall 32 and dispensing tube 42 may be attached and sealed together by an adhesive, such as a silicone or cyanoacrylate adhesive.

The second reactant 40 may be dispensed from the dispensing tube 42 into the cavity 31 by activating a plunger 44 (which can be seen in FIG. 1) located at a proximal end portion of the dispensing tube 42. The plunger 44 includes a plunger head 45 which forces the second reactant 40 into the cavity 31 of reaction chamber 30. Typically, the second reactant 40, prior to dispensing, is secured within the dispensing tube 42 by a breakable seal 46. Such seals should be selected to be made of a material that does not significantly degrade while in contact with the reactant materials.

As illustrated in FIG. 3, when the first and second reactants 33, 40 are mixed, they produce a product 48 which occupies a volume that is less than the volume occupied by the first reactant 33 prior to mixing. The reduction of the volume occupied by the material within the cavity 31 of the chamber 30 causes activation of the release action to deploy the occlusion device 28. Activation in this regard effects a reduction in the spacing between opposing inner surfaces 36. Such reduction in spacing can be caused by a decrease of the pressure within the cavity when the reduced volume product 48 creates a void that is filled by inward movement of the sidewall. Alternatively, or additionally, the product 48 can have adhesive-like properties to assist in such sidewall inward movement.

Preferably, the plunger head 45 has a sufficiently tight seal with the dispensing tube 42 to ensure that the cavity 31 is completely sealed and to maintain the pressure within the cavity after the reactants react. In the situation where a pressure difference assists in activation of the release action in response to the product reduced volume, the external pressure outside of the chamber 30 acts on the proximal wall 32 and the portion 37 of the gripper 22 defining the cavity to cause the lower Durometer proximal wall 32 and said portion 37 of the gripper to collapse inward, as illustrated in FIGS. 3 and 4. The higher Durometer distal wall 34 of the reaction chamber 30 is sufficiently rigid to resist the external pressure and substantially retains its original size and shape. The distal wall 34 can provide a fulcrum or pivot point 50 that assists in opening or expanding the gripping element 24 in an outward direction. In other words, the portion 37 of the gripper 22 which is proximal the distal wall 34 collapses inwardly. The collapsing of the portion 37 causes the gripping element 24, which is located distal the distal wall 34, to expand outwardly or open about fulcrum 50.

The first and second reactants 33, 40 can be any reactants that produce a product 48 that occupies a volume less than the first reactant 33. Preferably, the first and second reactants 33, 40 are substances in the gaseous phase which react to form a gas, solid or liquid product 48 that occupies a volume which is less than the volume occupied by the first reactant 33. Alternatively, the first reactant 33 can be a substance in the gaseous phase that reacts with the second reactant 40 (a substance in the gas, solid or liquid phase) to produce a liquid or solid product 48 that has a volume less than the first reactant 33. It is also contemplated that the first reactant 33 could be a substance in the liquid phase that reacts with the second reactant 40 (a substance in the gas, solid or liquid phase) to produce a solid product 48 that has a volume less than the first reactant.

In operation, the catheter 12 is inserted into the vasculature system of a patient and positioned at a preselected location within a blood vessel 13, typically in conjunction with other devices and professional procedures as generally known in the art. The delivery unit 14 is inserted into and advanced through the catheter 12. Once the desired location is reached, the delivery unit 14 is advanced, and/or the catheter 12 is moved in a retrograde manner, such that the delivery unit moves with respect to and within the catheter until the occlusion device 28 moves out of the distal end of the catheter. During the procedure and before the occlusion device 28 has been deployed, if it is determined that the distal end of the catheter 12 or the occlusion device 28 is not in the correct location, the occlusion device may be retrieved back into the distal end of the catheter by retracting the delivery unit 14 proximally or advancing the catheter distally. Once the occlusion device has been retrieved, the catheter and/or the occlusion device may be repositioned.

When the occlusion device 28 is in the correct position, the plunger 44 may be activated to break the seal 46 and to dispense the second reactant 40 into the cavity 31 of the reaction chamber 30 so that the first and second reactants 33, 40 mix within the cavity 31. Referring to FIG. 3, the first and second reactants 33, 40 react to form a product 48 which has a volume less than the volume of the first reactant 33 prior to mixing. As described above, the reduction of the volume of the material within the cavity 31 of chamber 30 typically causes the pressure within the cavity to decrease which in turn causes the proximal wall 32 and/or the sidewall 37 of the gripper defining the cavity to collapse. This collapsing action causes the gripping element 24 to pivot about fulcrum 50 and expand outwardly or open, thereby deploying the occlusive device.

Referring to FIG. 4, after the occlusive device has been deployed, the delivery unit 14 can be retracted back into the delivery catheter 12. If desired, the delivery unit 14 can be completely retracted from the catheter 12 and a new delivery unit having similar features can be advanced through the delivery catheter to deploy additional occlusion devices.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A vascular occlusion device deployment system, comprising:
    a vascular occlusion device having a protruding portion;
    a deployment unit comprising a pusher having a proximal end portion and a distal end portion;
    a gripper located at the distal end portion of the pusher, said gripper including an outwardly expandable gripping element for gripping the protruding portion of the vascular occlusion device;
    a collapsible reaction chamber located within said gripper, said chamber collapsing upon a reaction of at least a first reactant and a second reactant within an interior cavity of said chamber whereby the collapse of the chamber causes the gripping element to outwardly expand, releasing the protruding portion of the vascular occlusion device;
    the cavity of the collapsible chamber is defined by a polymeric proximal wall, a polymeric distal wall and a sidewall of the chamber, the distal wall being distal of the collapsible chamber and having a Durometer hardness higher than that of the proximal wall;

said higher Durometer hardness distal wall provides a fulcrum which assists in the outward expansion of the gripping element when the reaction chamber collapses; and the first reactant is a substance that is in the gaseous phase and occupies a first volume, and the first and second reactants react to produce a product that is a second substance in the gas, liquid or solid phase, said product occupying a second volume that is less than the volume occupied by the first reactant to thereby effect the reaction chamber collapse and outward expansion of the gripping element to release the vascular occlusion device.

2. The deployment system of claim 1 wherein the proximal wall and the sidewall of the chamber collapse upon the reacting of at least the first reactant and the second reactant.

3. The deployment system of claim 1 wherein the gripping element comprises a plurality of jaws.

4. The deployment system of claim 1 further including a dispensing unit for dispensing the second reactant into the cavity of said reaction chamber.

5. The deployment system of claim 4 wherein the dispensing unit comprises a plunger operated dispensing tube.

6. A vascular occlusion device deployment system for deploying a vascular occlusion device at a preselected site within the vasculature of a patient, comprising:
  a deployment unit comprising a pusher having a proximal end portion and a distal end portion;
  a gripper located at the distal end portion of the pusher, said gripper including an outwardly expandable gripping element for gripping a vascular occlusion device;
  a collapsible chamber located for engagement with said gripper, said chamber having a first internal pressure prior to deployment of a vascular occlusion device;
  said collapsible chamber having a second internal pressure that is less than the first internal pressure which causes the collapsible chamber to collapse;
  the collapsible chamber is defined by a proximal wall, a distal wall and a portion of the pusher or the gripper, the distal wall being distal of the collapsible chamber and having a Durometer hardness higher than that of the proximal wall;
  said higher Durometer hardness distal wall provides a fulcrum which assists in outward expansion of the gripping element when the collapsible chamber collapses; and
  the collapsible chamber houses a first reactant that creates the first internal pressure and a second reactant that reacts with the first reactant within said chamber to form a product that creates the second internal pressure, the product occupying a volume which is less than the volume of the first reactant;
  whereby upon collapsing of said collapsible chamber said chamber causes the gripping element to expand outwardly for releasing a vascular occlusion device therefrom.

7. The deployment system of claim 6 wherein the first reactant is a substance that is in the gaseous phase and has a first volume, and the first and second reactants react to produce a product that is a second substance in the gas, liquid or solid phase, said product having a second volume less than the volume of the first reactant.

8. The deployment system of claim 6 further including a dispensing unit for dispensing the second reactant into the collapsible chamber.

9. The deployment system of claim 8 wherein the dispensing unit comprises a plunger operated dispensing tube.

10. The deployment system of claim 6 wherein the proximal wall and the portion of the pusher or the gripper collapse when the collapsible chamber has the second internal pressure.

11. The deployment system of claim 6 wherein the gripping elements comprise a plurality of jaws.

12. A method for deployment of a vascular occlusion device at a preselected location within the vasculature of a patient, comprising:
  providing a deployment unit comprising a pusher member having a gripper located at a distal end of the pusher member, said gripper having an expandable gripping element for gripping a vascular occlusion device and a collapsible reaction chamber disposed within said gripper and having a proximal wall and a distal wall of a Durometer hardness higher than that of the proximal wall, the distal wall being distal of the reaction chamber, said collapsible reaction chamber housing a first reactant occupying a first volume;
  gripping a protruding portion of a vascular occlusion device with said gripper;
  guiding the vascular occlusion device to a preselected location within the vasculature of a patient with said pusher;
  collapsing the collapsible chamber by mixing a second reactant with the first reactant within the collapsible reaction chamber to produce a product that occupies a second volume that is less than the first volume occupied by the first reactant; and
  expanding the gripping element under the force of the collapsible reaction chamber while the distal wall provides a fulcrum effect assist, thereby releasing the protruding portion of the vascular occlusion device.

13. The method of claim 12 wherein the mixing said second reactant with said first reactant comprises dispensing the second reactant into the cavity through a dispensing tube.

* * * * *